(12) United States Patent
Hagenbuch et al.

(10) Patent No.: US 11,152,087 B2
(45) Date of Patent: Oct. 19, 2021

(54) ENSURING QUALITY IN ELECTRONIC HEALTH DATA

(71) Applicant: International Business Machines Corporation, Armonk, NY (US)

(72) Inventors: Matthew Hagenbuch, Cleveland, OH (US); Yifan Xu, Cleveland, OH (US); James Natale, Cleveland, OH (US); Matthew M. Pohlman, Shaker Heights, OH (US)

(73) Assignee: International Business Machines Corporation, Armonk, NY (US)

( * ) Notice: Subject to any disclaimer, the term of this patent is extended or adjusted under 35 U.S.C. 154(b) by 194 days.

(21) Appl. No.: 16/158,695

(22) Filed: Oct. 12, 2018

(65) Prior Publication Data

US 2020/0118653 A1 Apr. 16, 2020

(51) Int. Cl.
*G16H 10/60* (2018.01)
*G16H 50/30* (2018.01)
(Continued)

(52) U.S. Cl.
CPC ............ *G16H 10/60* (2018.01); *G16H 50/30* (2018.01); *G06Q 10/06395* (2013.01);
(Continued)

(58) Field of Classification Search
CPC ........ G16H 10/60; G16H 50/30; G16H 10/20; G16H 80/00; G06Q 30/04; G06Q 10/6395
(Continued)

(56) References Cited

U.S. PATENT DOCUMENTS 8,721,706 B2 * 5/2014 Jung ...................... G06Q 10/06
623/1.15
8,862,485 B2 10/2014 Duncan et al.
(Continued)

OTHER PUBLICATIONS

Weiskopf et al., "Methods and Dimensions of Electronic Health Record Data Quality Assessment: Enabling Reuse for Clinical Research," Journal of the American Medical Informatics Association, vol. 20, No. 1, 2013, pp. 144-151.
(Continued)

*Primary Examiner* — Michael Tomaszewski
*Assistant Examiner* — Rachael Sojin Stone
(74) *Attorney, Agent, or Firm* — Robert A. Voigt, Jr.; Winstead PC

(57) ABSTRACT

A method, system and computer program product for ensuring quality in electronic health data. Data processing pipelines among different tenants are monitored for data artifacts generated from electronic health data, where a "data artifact" refers to the tangible by-products produced during the processing of the electronic health record datasets generated by the electronic health record systems as well as the datasets themselves. Out of the generated data artifacts, those data artifacts that are produced from the same stage of the data processing pipelines among the different tenants are aggregated. A set of metrics at various levels of a dataset hierarchy are produced from the aggregated data artifacts. Such metrics provide information about a quality of the electronic health data. A quality report, which may include flagged issues with the datasets, is then generated and presented to a user based on an analysis of the produced set of metrics.

20 Claims, 9 Drawing Sheets

(51) Int. Cl.
*G16H 80/00* (2018.01)
*G06Q 30/04* (2012.01)
*G16H 10/20* (2018.01)
*G06Q 10/06* (2012.01)

(52) U.S. Cl.
CPC ............ *G06Q 30/04* (2013.01); *G16H 10/20* (2018.01); *G16H 80/00* (2018.01)

(58) Field of Classification Search
USPC .......................................................... 705/3
See application file for complete search history.

(56) References Cited

U.S. PATENT DOCUMENTS

| | | | | |
|---|---|---|---|---|
| 10,404,549 | B2* | 9/2019 | Gopalan | ............ H04L 41/0893 |
| 2008/0097789 | A1 | 4/2008 | Huffer | |
| 2014/0316810 | A1 | 10/2014 | Oliver et al. | |
| 2015/0302436 | A1* | 10/2015 | Reynolds | ........... G06Q 30/0201 |
| | | | | 705/7.32 |
| 2016/0048655 | A1* | 2/2016 | Maitra | ................... G16H 20/10 |
| | | | | 705/3 |
| 2017/0257669 | A1* | 9/2017 | Liu | .................... H04N 21/2668 |
| 2017/0300540 | A1* | 10/2017 | Karpistsenko | .... H04L 29/06027 |
| 2018/0130003 | A1 | 5/2018 | Sublett et al. | |

OTHER PUBLICATIONS

Kaushal et al., "Developing and Using Valid Clinical Quality Metrics for HIT and HIE," Submitted to: The Agency for Healthcare Research and Quality (AHRQ) U.S. Department of Health and Human Services, 2011, pp. 1-20.
Kern et al., "Electronic Health Records and Health Care Quality Over Time in a Federally Qualified Health Center," Journal of the American Medical Informatics Association, vol. 22, No. 2, 2015, pp. 453-458.
David W. Bates, "Getting in Step: Electronic Health Records and their Role in Care Coordination," Journal of General Internal Medicine, vol. 25, No. 3, pp. 174-176.
Glad J. Kuperman, "Health-Information Exchange: Why are we Doing it, and What are we Doing?," Journal of the American Medical Informatics Association, vol. 18, No. 5, 2011, pp. 678-682.
Casalino et al., "US Physician Practices Spend More Than $15.4 Billion Annually to Report Quality Measures," Health Affairs, vol. 35, No. 3, 2016, pp. 401-406.

* cited by examiner

| ALERTS | ALL | | | | | SEARCH: CLAIMS_PP_GAMMA | | |
|---|---|---|---|---|---|---|---|---|
| SHOW: 10 | | | | | | | | |
| 10-DAY TREND △ | METRIC | VALUE | SOURCE SYSTEM ID | SOURCE SYSTEM QUALIFIER | SOURCE DATA TYPE | FIELD | FILL (%) | |
| 100k — 95.2k | COUNT | 98197.00 | CLAIMS_PP_GAMMA | DEMOG | DEMOGRAPHIC.V2 | gender | 98.2k/98.2k | |
| 100 — 100 | FILL (%) | 100.00 | CLAIMS_PP_GAMMA | DEMOG | DEMOGRAPHIC.V2 | gender | 98.2k/98.2k | |
| 2.00 — 2.00 | N-CAT 100 | 2.00 | CLAIMS_PP_GAMMA | DEMOG | DEMOGRAPHIC.V2 | gender | 98.2k/98.2k | |
| 2.00 — 2.00 | N-CAT 90 | 2.00 | CLAIMS_PP_GAMMA | DEMOG | DEMOGRAPHIC.V2 | gender | 98.2k/98.2k | |
| 90.1k — 49.4k | COUNT | 49373.00 | CLAIMS_PP_GAMMA | DEMOG | DEMOGRAPHIC.V2 | postalCode | 49.4k/98.2k | |
| 90.1 — 50.3 | FILL (%) | 50.28 | CLAIMS_PP_GAMMA | DEMOG | DEMOGRAPHIC.V2 | postalCode | 49.4k/98.2k | |
| 3.15k — 2.5k | N-CAT 100 | 2841.00 | CLAIMS_PP_GAMMA | DEMOG | DEMOGRAPHIC.V2 | postalCode | 49.4k/98.2k | |
| 270 — 190 | N-CAT 90 | 270.00 | CLAIMS_PP_GAMMA | DEMOG | DEMOGRAPHIC.V2 | postalCode | 49.4k/98.2k | |
| 100k — 99.2k | COUNT | 98197.00 | CLAIMS_PP_GAMMA | DEMOG | DEMOGRAPHIC.V2 | firstName | 98.2k/98.2k | |
| 100 — 100 | FILL (%) | 100.00 | CLAIMS_PP_GAMMA | DEMOG | DEMOGRAPHIC.V2 | firstName | 98.2k/98.2k | |

SHOWING 1 TO 10 OF 32 ENTRIES (FILTERED FROM 444 TOTAL ENTRIES)   PREVIOUS 1 2 3 4 NEXT

FIG. 8B

ENSURING QUALITY IN ELECTRONIC HEALTH DATA

TECHNICAL FIELD

The present invention relates generally to electronic health records, and more particularly to ensuring quality in electronic health data.

BACKGROUND

An electronic health record (EHR) is the systematized collection of patient and population electronically-stored health information in a digital format. These records can be shared across different health care settings. Records are shared through network-connected, enterprise-wide information systems or other information networks and exchanges. EHRs may include a range of data, including demographics, medical history, medication and allergies, immunization status, laboratory test results, radiology images, vital signs, personal statistics, such as age and weight, and billing information.

Ensuring good data quality in such records is essential due to the types of information stored in such records which are used to ensure the wellbeing of patients. However, defining and measuring quality in such records is challenging, especially in a multitenant analytical platform (e.g., multiple healthcare systems), due to several factors, such as the large data volume. There are hundreds of millions of EHRs being generated every day from healthcare systems.

Furthermore, defining and measuring quality in such records is challenging because of the heterogeneous data sources. Different hospitals often use distinctive EHR systems that adopt various formats. Even within the same hospital, different departments may generate duplicate or contradicting records. Thus, the standard of quality of EHR varies based on the data sources.

Additionally, defining and measuring quality in such records is challenging because of complex relations among variables. For example, there are millions of codes from standard ontologies (International Classification of Diseases (ICD), Systematized Nomenclature of Medicine (SNOMED®), RxNorm®, Common Procedure Terminology (CPT®), Logical Observation Identifiers Names and Codes (LOINC®), etc.) that describe diagnoses, medical procedures, lab tests, and drugs, not to mention countless custom codes.

Further, defining and measuring quality in such records is challenging because of operational factors, such as utilizing multiple data processing pipelines that are each configured per tenant, regularly receiving new data and utilizing a continuous delivery development model. These complications may introduce quality issues unrelated to the source data quality.

Hence, there is not currently a means for ensuring quality in the electronic health data.

SUMMARY

In one embodiment of the present invention, a method for ensuring quality in electronic health data comprises monitoring data processing pipelines among different tenants for data artifacts generated from electronic health data, where the data processing pipelines comprise a set of data processing elements connected in series where an output of one element is an input of a next element, where the data processing pipelines comprise stages of different processing, and where the generated data artifacts comprise tangible by-products produced during processing of electronic health record datasets as well as the datasets themselves. The method further comprises aggregating data artifacts of the generated data artifacts produced from a same stage of the data processing pipelines among the different tenants. The method additionally comprises producing a set of metrics at various levels of a dataset hierarchy from the aggregated data artifacts, where the produced set of metrics provides information about a quality of the electronic health data. Furthermore, the method comprises analyzing the produced set of metrics to generate aggregate outputs, where the aggregate outputs comprise one or more of the following: classified trends based on computing rollup values along several dimensions for different time intervals resulting in a superset containing both original single-metric trends and computed aggregate trends and then classifying each trend using a set of mathematical tests, grouped datasets by aggregating trend classifications identified in an output for each group and identified trends for the group as a whole, and configured checklists based on platform input limitations at each stage of the data processing pipelines among the different tenants. Furthermore, the method comprises generating a quality report based on the aggregate outputs. Additionally, the method comprises presenting the quality report to a user.

Other forms of the embodiment of the method described above are in a system and in a computer program product.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE DRAWINGS

A better understanding of the present invention can be obtained when the following detailed description is considered in conjunction with the following drawings, in which:

FIGS. 8A-8B show a screen capture of a tenant-level data change report targeted toward internal users monitoring data quality changes across tenants in accordance with an embodiment of the present invention.

DETAILED DESCRIPTION

The present invention comprises a method, system and computer program product for ensuring quality in electronic health data. In one embodiment of the present invention, data processing pipelines among different tenants are monitored for data artifacts generated from electronic health data. A "data artifact," as used herein, refers to the tangible by-products produced during the processing of the electronic health record datasets generated by the electronic health record systems as well as the datasets themselves. Out of the generated data artifacts, those data artifacts that are produced from the same stage of the data processing pipelines among the different tenants are aggregated. A set of metrics at various levels of a dataset hierarchy are produced from the aggregated data artifacts. In one embodiment, such metrics provide information about a quality of the electronic health data. The set of metrics are then analyzed to generate aggregate outputs, which may include: (1) the classified trends based on computing rollup values along several dimensions for different time intervals resulting in a superset containing both original single-metric trends and computed aggregate trends and then classifying each trend using a set of mathematical tests, (2) grouped datasets by aggregating trend classifications identified in an output for each group and identified trends for the group as a whole and/or (3) configured checklists based on platform input limitations at each stage of the data processing pipelines among the different tenants. A quality report is generated based on the aggregate outputs. Such a quality report may include flagged issues with the datasets. The quality report is then presented to the user. In this manner, the present invention ensures quality in the electronic health data.

In the following description, numerous specific details are set forth to provide a thorough understanding of the present invention. However, it will be apparent to those skilled in the art that the present invention may be practiced without such specific details. In other instances, well-known circuits have been shown in block diagram form in order not to obscure the present invention in unnecessary detail. For the most part, details considering timing considerations and the like have been omitted inasmuch as such details are not necessary to obtain a complete understanding of the present invention and are within the skills of persons of ordinary skill in the relevant art.

Figure 1:
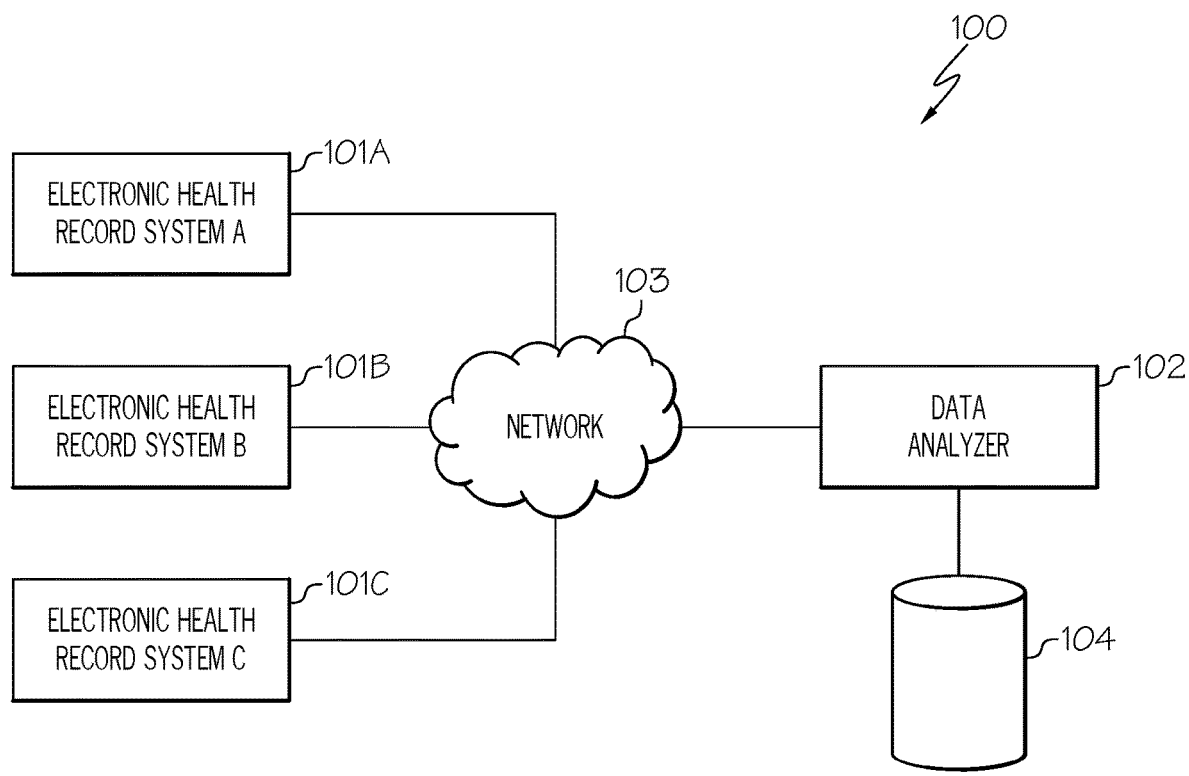
FIG. 1 illustrates a communication system for practicing the principles of the present invention in accordance with an embodiment of the present invention.

Referring now to the Figures in detail, FIG. 1 illustrates an embodiment of the present invention of a communication system 100 for practicing the principles of the present invention in accordance with an embodiment of the present invention. Communication system 100 includes electronic health record systems 101A-101C (identified as "Electronic Health Record System A," "Electronic Health Record System B," and "Electronic Health Record System C," respectively, in FIG. 1) connected to a data analyzer 102 via a network 103. Electronic health record systems 101A-101C may collectively or individually be referred to as electronic health record systems 101 or electronic health record system 101, respectively.

Healthcare systems generate a large volume of electronic health records (EHRs) via electronic health record systems 101, which may be shared across different health care settings. A "healthcare system," as used herein, refers to the organization of people, institutions and resources that deliver health care services to meet the health needs of target populations. Such systems utilize electronic health record systems 101 configured to generate EHRs directed to the health services provided by the healthcare systems. These records are shared through network-connected, enterprise-wide information systems or other information networks and exchanges, such as via network 103. EHRs may include a range of data, including demographics, medical history, medication and allergies, immunization status, laboratory test results, radiology images, vital signs, personal statistics, such as age and weight, and billing information.

Different healthcare systems may use distinctive EHR systems 101 that adopt various formats. Even within the same healthcare care system, different departments may generate duplicate or contradicting records. As a result, defining and measuring quality in such records is challenging because of heterogeneous data sources.

Furthermore, as discussed in the Background section, defining and measuring quality in such records is also challenging because of the large data volume, the complex relations among variables and the operational factors.

Hence, there is not currently a means for ensuring quality in the electronic health data.

Data analyzer 102, as shown in FIG. 1, is configured to ensure quality in the electronic health data generated by electronic health record systems 101 by tracking and analyzing many quality metrics measured against the EHR datasets generated by electronic health record systems 101 at multiple stages of the data processing pipelines for the multiple tenants (e.g., multiple healthcare systems) as discussed below in connection with FIGS. 3-7 and 8A-8B. A description of the hardware configuration of data analyzer 102 is provided below in connection with FIG. 2.

Network 103 may be, for example, a local area network, a wide area network, a wireless wide area network, a circuit-switched telephone network, a Global System for Mobile Communications (GSM) network, a Wireless Application Protocol (WAP) network, a WiFi network, an IEEE 802.11 standards network, various combinations thereof, etc. Other networks, whose descriptions are omitted here for brevity, may also be used in conjunction with system 100 of FIG. 1 without departing from the scope of the present invention.

Furthermore, as shown in FIG. 1, data analyzer 102 is connected to a database 104. In one embodiment, database 104 is configured to store the historical values for the metrics (also referred to herein as the "standard set of metrics") obtained from previously generated data artifacts. In one embodiment, the standard set of metrics is provided by a user. A "metric," as used herein, refers to the measurement of a particular characteristic of the processing of electronic health data in a data processing pipeline for a tenant. A "data artifact," as used herein, refers to the tangible by-products produced during the processing of the electronic health record datasets generated by electronic health record systems 101 as well as the datasets themselves. A further discussion regarding metric history and data artifacts are provided further below.

System 100 is not to be limited in scope to any one particular network architecture. System 100 may include any number of electronic health record systems 101, data analyzers 102, networks 103 and databases 104. Furthermore, while FIG. 1 illustrates data analyzer 102 as being a separate physical device, some or all of the functionality of data analyzer 102 may reside within electronic health record system 101.

Figure 2:
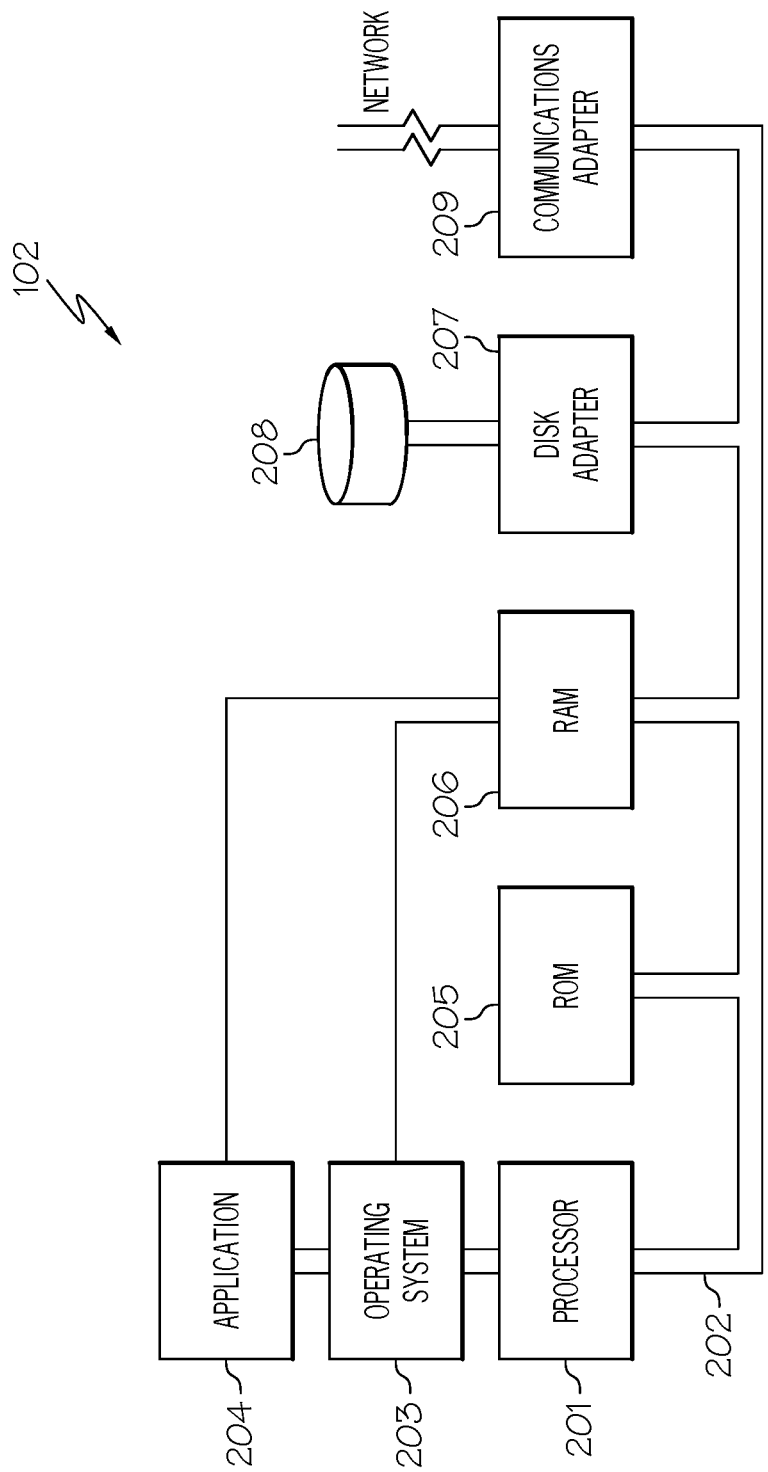
FIG. 2 illustrates an embodiment of the present invention of a hardware configuration of a data analyzer which is representative of a hardware environment for practicing the present invention.

Referring now to FIG. 2, FIG. 2 illustrates a hardware configuration of data analyzer 102 (FIG. 1) which is representative of a hardware environment for practicing the present invention. Referring to FIG. 2, data analyzer 102 has a processor 201 coupled to various other components by system bus 202. An operating system 203 runs on processor 201 and provides control and coordinates the functions of the various components of FIG. 2. An application 204 in accordance with the principles of the present invention runs in conjunction with operating system 203 and provides calls to operating system 203 where the calls implement the various functions or services to be performed by application 204. Application 204 may include, for example, a program for ensuring quality in electronic health data as discussed below in association with FIGS. 3-7 and 8A-8B.

Referring again to FIG. 2, read-only memory ("ROM") 205 is coupled to system bus 202 and includes a basic input/output system ("BIOS") that controls certain basic functions of data analyzer 102. Random access memory ("RAM") 206 and disk adapter 207 are also coupled to system bus 202. It should be noted that software components including operating system 203 and application 204 may be loaded into RAM 206, which may be data analyzer's 102 main memory for execution. Disk adapter 207 may be an integrated drive electronics ("IDE") adapter that communicates with a disk unit 208, e.g., disk drive. It is noted that the program for ensuring quality in electronic health data, as discussed below in association with FIGS. 3-7 and 8A-8B, may reside in disk unit 208 or in application 204.

Data analyzer 102 may further include a communications adapter 209 coupled to bus 202. Communications adapter 209 interconnects bus 202 with an outside network (e.g., network 103 of FIG. 1) thereby allowing data analyzer 102 to communicate with electronic health record systems 101.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As stated in the Background section, ensuring good data quality in such records is essential due to the types of information stored in such records which are used to ensure the wellbeing of patients. However, defining and measuring quality in such records is challenging, especially in a multitenant analytical platform (e.g., multiple healthcare systems), due to several factors, such as the large data volume. There are hundreds of millions of EHRs being generated every day from healthcare systems. Furthermore, defining and measuring quality in such records is challenging because of the heterogeneous data sources. Different hospitals often use distinctive EHR systems that adopt various formats. Even within the same hospital, different departments may generate duplicate or contradicting records. Thus, the standard of quality of EHR varies based on the data sources. Additionally, defining and measuring quality in such records is challenging because of complex relations among variables. For example, there are millions of codes from standard ontologies (International Classification of Diseases (ICD), Systematized Nomenclature of Medicine (SNOMED®), RxNorm®, Common Procedure Terminology (CPT®), Logical Observation Identifiers Names and Codes (LOINC®), etc.) that describe diagnoses, medical procedures, lab tests, and drugs, not to mention countless custom codes. Further, defining and measuring quality in such records is challenging because of operational factors, such as utilizing multiple data processing pipelines that are each configured per tenant, regularly receiving new data and utilizing a continuous delivery development model. These complications may introduce quality issues unrelated to the source data quality. Hence, there is not currently a means for ensuring quality in the electronic health data.

Figure 3:
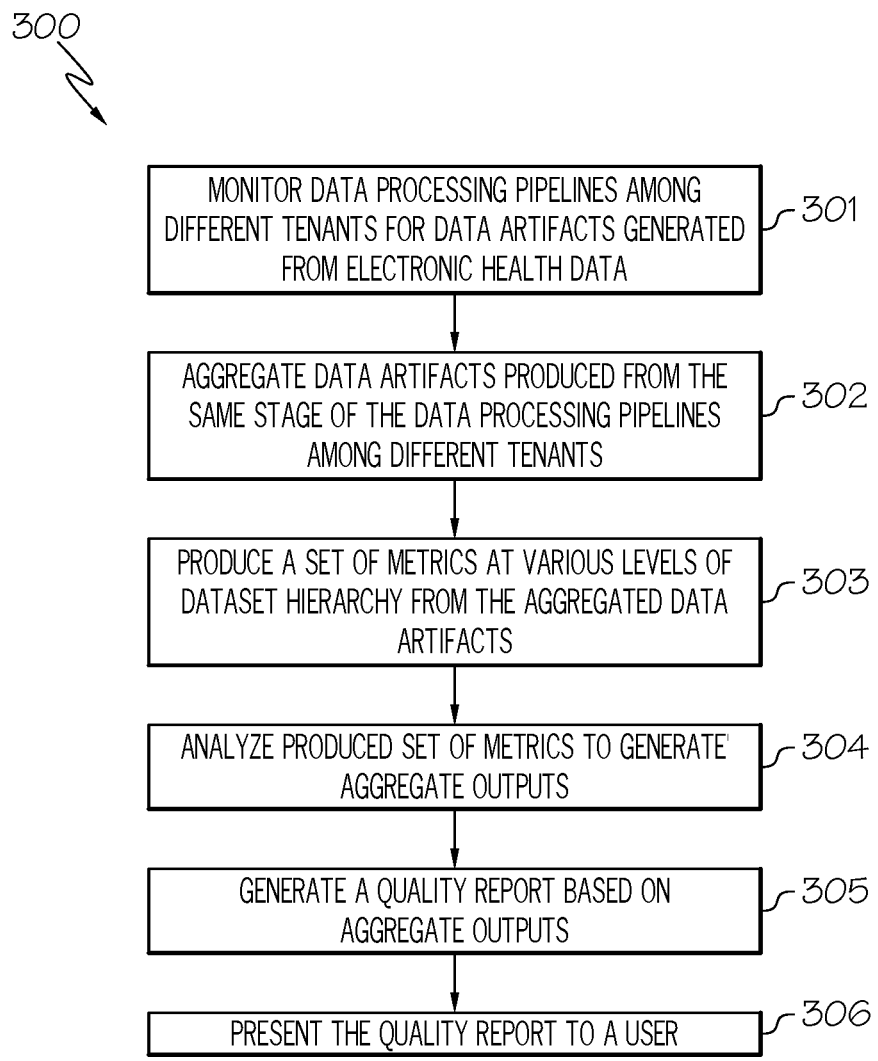
FIG. 3 is a flowchart of a method for ensuring quality in electronic health data in accordance with an embodiment of the present invention.
Figure 4:
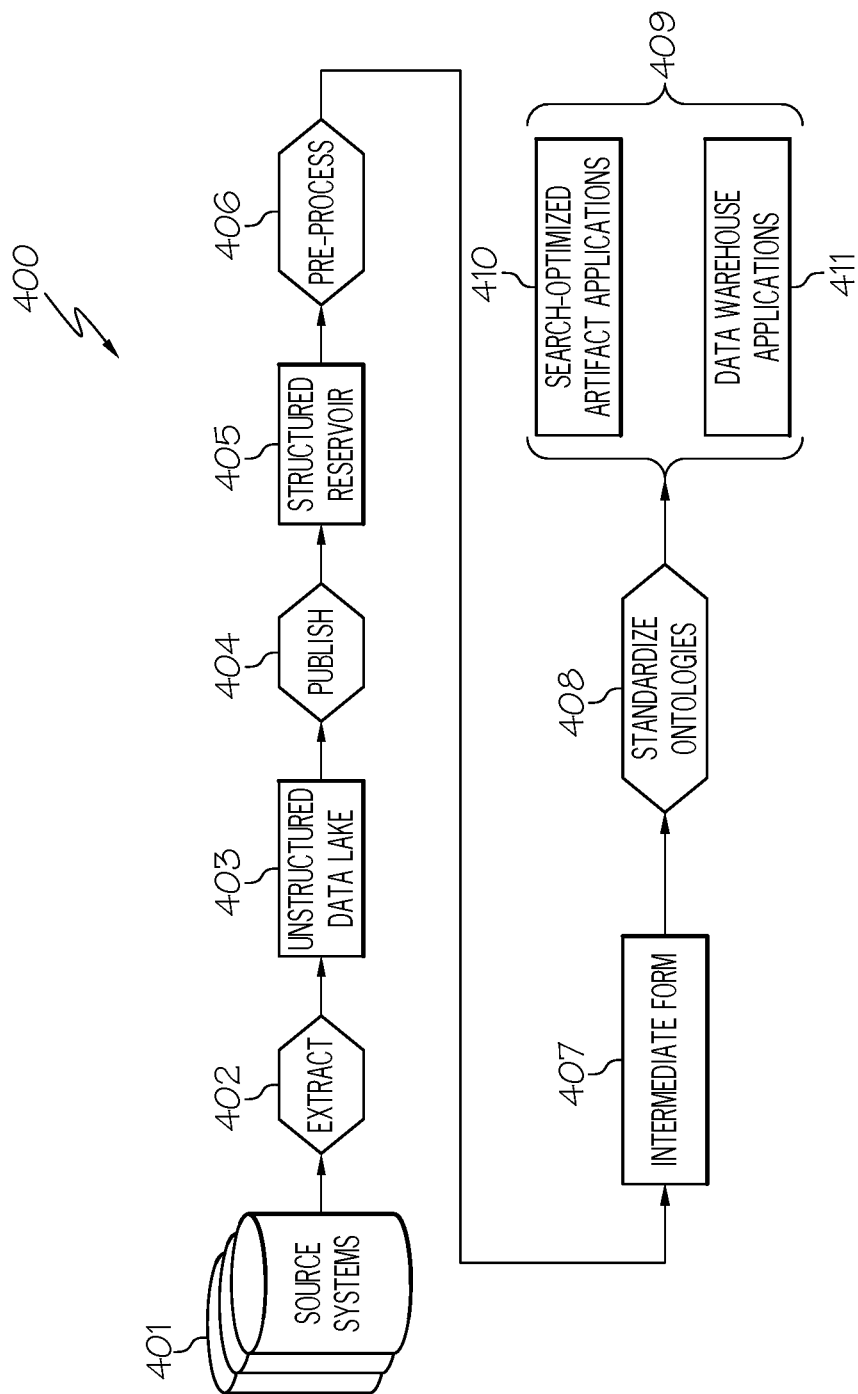
FIG. 4 illustrates a data processing pipeline for a single tenant in accordance with an embodiment of the present invention.
Figure 5:
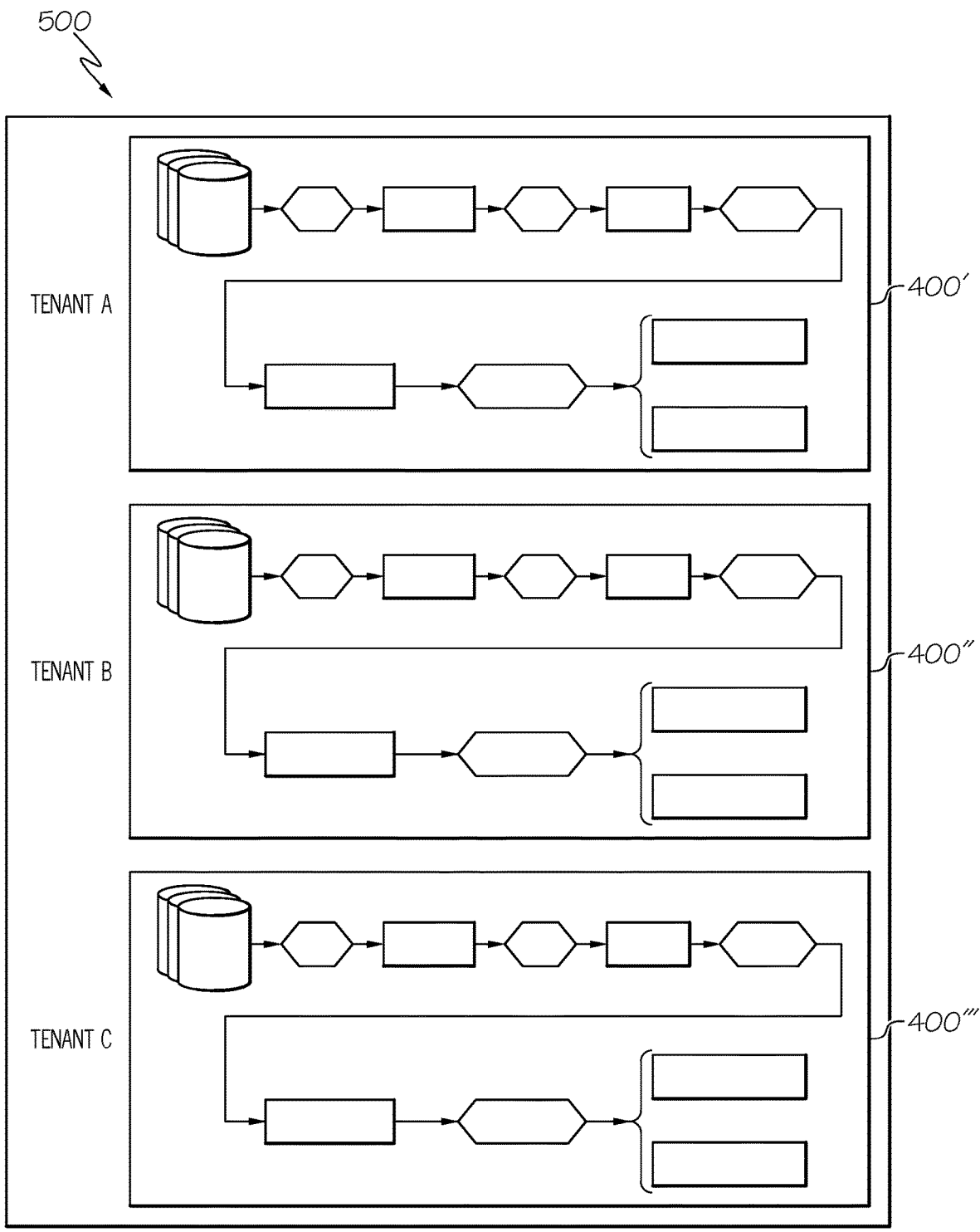
FIG. 5 illustrates a platform for a multi-tenancy model, where each tenant is associated with a separate processing pipeline that generates a separate set of data artifacts, in accordance with an embodiment of the present invention.
Figure 6:
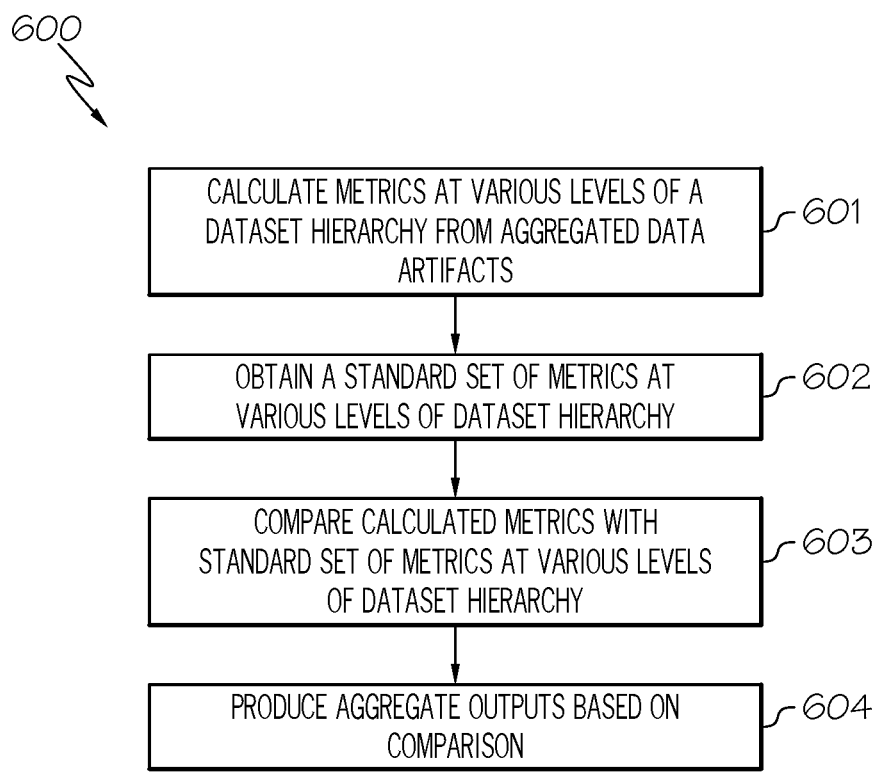
FIG. 6 is a flowchart of a method for generating the aggregate outputs in accordance with an embodiment of the present invention.
Figure 7:
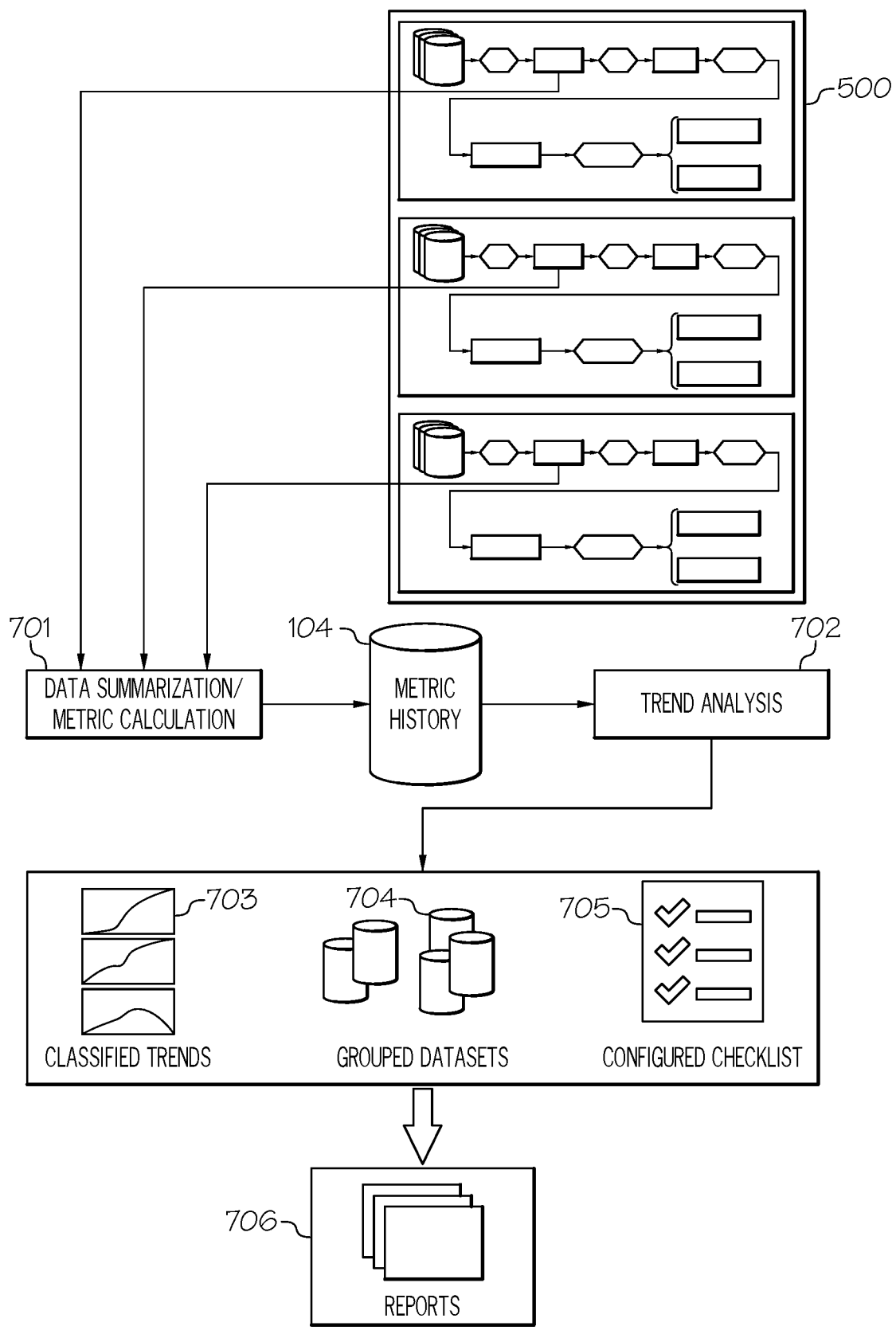
FIG. 7 illustrates applying a quality measurement process to each data artifact in accordance with an embodiment of the present invention.
Figure 8A:
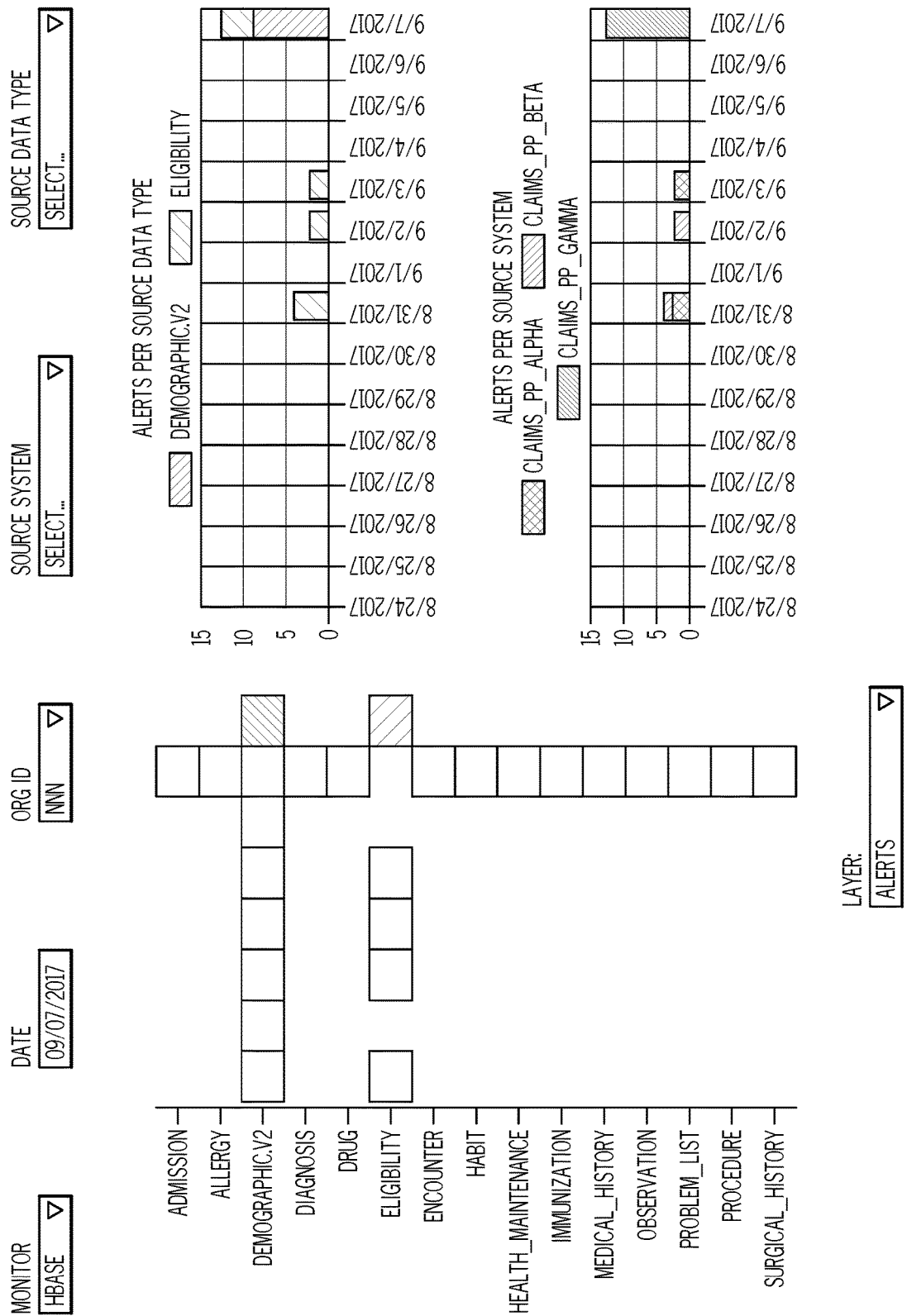

The embodiments of the present invention provide a means for ensuring quality in the electronic health data by tracking and analyzing many quality metrics measured against the electronic health record datasets generated by electronic health record systems 101 (FIG. 1) at multiple stages of the data processing pipeline as discussed below in connection with FIGS. 3-7 and 8A-8B. FIG. 3 is a flowchart of a method for ensuring quality in electronic health data. FIG. 4 illustrates a data processing pipeline for a single tenant. FIG. 5 illustrates a platform for a multi-tenancy model, where each tenant is associated with a separate processing pipeline that generates a separate set of data artifacts. FIG. 6 is a flowchart of a method for generating the aggregate outputs. FIG. 7 illustrates applying a quality measurement process to each data artifact. FIGS. 8A-8B show a screen capture of a tenant-level data change report targeted toward internal users monitoring data quality changes across tenants.

As stated above, FIG. 3 is a flowchart of a method 300 for ensuring quality in electronic health data in accordance with an embodiment of the present invention.

Referring to FIG. 3, in conjunction with FIGS. 1-2, in step 301, data analyzer 102 monitors the data processing pipelines among different tenants (e.g., healthcare systems) for data artifacts generated from electronic health data. Each data processing pipeline may generate data artifacts from the same or different electronic health data, including electronic health data that includes different types of electronic health records (e.g., radiology images, laboratory test results) for the same patient.

A "data processing pipeline," as used herein, refers to a set of data processing elements connected in series where an output of one element is an input of a next element as discussed below in connection with FIG. 4. Furthermore, the data processing pipelines include stages of different processing as discussed below in connection with FIG. 4.

Referring to FIG. 4, FIG. 4 illustrates a data processing pipeline 400 for a single tenant (e.g., healthcare system) in accordance with an embodiment of the present invention. As shown in FIG. 4, data processing pipeline 400 includes various data processing elements connected in series where an output of one element is an input of a next element. For example, data processing pipeline 400 includes multiple source systems 401. That is, each tenant's (e.g., a particular healthcare system) dataset consists of multiple source systems 401. An example of a source system is the Epic Clarity EHR system at the Cleveland Clinic Main Campus for the Cleveland Clinic tenant.

Furthermore, as shown in FIG. 4, the source system data 401 is extracted 402, where in its unstructured form, it is stored in unstructured data lake 403 (data lake is a system or repository of data stored in its natural format, usually object blobs or files). In one embodiment, unstructured data lake 403 is maintained in a storage unit (e.g., memory 205, disk unit 208) in data analyzer 102. Alternatively, such information may be stored in database 104.

Additionally, as shown in FIG. 4, the unstructured data 403 is published 404, where in its structured form, it is stored in structured reservoir 405. In one embodiment, structured reservoir 405 is maintained in a storage unit (e.g., memory 205, disk unit 208) in data analyzer 102. Alternatively, such information may be stored in database 104.

After pre-processing 406 the structured data 405, an intermediate form 407 of the health data is formed. In one embodiment, the intermediate form 407 of the health data is stored in a storage unit (e.g., memory 205, disk unit 208) of data analyzer 102 or in database 104.

Standardized ontologies 408 are applied to the intermediate form 407 of the health data thereby producing data store applications 409, such as search-optimized artifact applications 410 and data warehouse applications 411.

As shown in FIG. 4, data processing pipeline 400 begins with the extraction 402 of source system data 401 and terminates with data store applications 409. Elements 401, 403, 405, 407 and 409 (includes elements 410, 411) represent a data artifact which persists beyond process execution. A "data artifact," as used herein, refers to the tangible by-products produced during the processing of the electronic health record datasets generated by electronic health record systems 101 as well as the datasets themselves. Furthermore, as shown in FIG. 4, data processing pipeline 400 includes stages of different processing, such as extraction 402, publication 404, pre-processing 406 and applying standard ontologies 408.

As discussed above, in one embodiment, data analyzer 102 monitors the data processing pipelines among different tenants (e.g., healthcare systems) for data artifacts generated from electronic health data as shown in FIG. 5.

FIG. 5 illustrates a platform for a multi-tenancy model 500, where each tenant is associated with a separate processing pipeline that generates a separate set of data artifacts, in accordance with an embodiment of the present invention.

Referring to FIG. 5, multi-tenancy model 500 includes multiple data processing pipelines 400', 400", 400'" corresponding to data processing pipeline 400 of FIG. 4. Data processing pipeline 400' corresponds to the data processing pipeline for Tenant A (e.g., Cleveland Clinic) as shown in FIG. 5. Furthermore, data processing pipeline 400" corresponds to the data processing pipeline for Tenant B (e.g., Mayo Clinic) as shown in FIG. 5. Additionally, data processing pipeline 400'" corresponds to the data processing pipeline for Tenant C (e.g., UNC Healthcare) as shown in FIG. 5. While FIG. 5 illustrates monitoring three data processing pipelines for three tenants, the principles of the present invention are not to be limited in scope to monitoring only three data processing pipelines for three tenants. Instead, the principles of the present invention are to include the aspect of monitoring any number of data processing pipelines for any number of tenants.

As shown in FIG. 5, data analyzer 102 processes electronic health data from each tenant in a separate pipeline on the platform. The processing modules within each pipeline are configured and customized for each tenant. Each tenant pipeline generates a separate set of data artifacts as discussed above in connection with FIG. 4. In one embodiment, the data artifacts generated by different tenant pipelines are from the same or different electronic health data, including electronic health data that includes different types of electronic health records (e.g., radiology images, laboratory test results) for the same patient.

In one embodiment, data analyzer 102 efficiently monitors the processing pipelines 400', 400" and 400'" for both source data quality and data processing issues. In one embodiment, data analyzer 102 efficiently triages data quality issues to produce consumable quality reports which lead to actionable investigations and resolutions at a system level as discussed below. In order to produce such quality reports, a quality measurement process is applied to each data artifact in the pipeline 400', 400" and 400'" as discussed further below.

Returning to FIG. 3, in conjunction with FIGS. 1-2 and 4-5, in step 302, data analyzer 102 aggregates the data artifacts (e.g., element 407) produced from the same stage (e.g., pre-processing 406) of the data processing pipelines (e.g., processing pipelines 400', 400" and 400'") among different tenants (e.g., tenants A, B and C). In this manner, the behavior across datasets can be compared to flag unexpected changes. For example, inaccuracies in personal statistics about a patient may be identified among different electronic health records processed by different tenants.

In step 303, data analyzer 102 produces a set of metrics at various levels of a dataset hierarchy from the aggregated data artifacts. A "metric," as used herein, refers to the measurement of a particular characteristic of the processing of electronic health data in a data processing pipeline for a tenant. For example, data analyzer 102 may produce a set of clinical metrics pertaining to the unstructured data 403 of the electronic health data. For instance, metrics, such as record type, date of record, data values, data models, data presentation, and conformance with governance policies, may be calculated at various levels of the dataset hierarchy (e.g., database, file, record, field). In one embodiment, the set of metrics is continuously calculated as new data is ingested and as existing data is reprocessed. In one embodiment, such metrics provide information about a quality of the electronic health data, such as identifying inconsistent data values (e.g., social security numbers) among different health records for the same patient.

In step 304, data analyzer 102 analyzes the produced set of metrics to generate aggregate outputs. For example, the outputs may include: (1) the classified trends based on computing rollup values along several dimensions for different time intervals resulting in a superset containing both original single-metric trends and computed aggregate trends and then classifying each trend using a set of mathematical tests, (2) grouped datasets by aggregating trend classifications identified in an output for each group and identified trends for the group as a whole and/or (3) configured checklists based on platform input limitations at each stage of the data processing pipelines among the different tenants as discussed further below in connection with FIGS. 6 and 7.

FIG. 6 is a flowchart of a method 600 for generating the aggregate outputs. FIG. 7 illustrates applying a quality measurement process to each data artifact in accordance with an embodiment of the present invention.

Referring to FIG. 6, in conjunction with FIGS. 4-5 and 7, in step 601, data analyzer 102 produces or calculates the metrics at various levels of the dataset hierarchy (e.g., organization of data in a hierarchy with multiple levels, such as database, file, record and field) from the aggregated data artifacts as discussed above in connection with step 303. For example, data artifacts are aggregated from the same stage of the processing pipelines 400', 400" and 400'" of multi-tenancy model 500 by data analyzer 102 to perform data summarization/metric calculation 701. For instance, data summarization/metric calculation 701 may include metrics (e.g., clinical metrics) pertaining to the unstructured data 403 of the electronic health data. For example, metrics, such as record type, date of record, data values, data models, data presentation, and conformance with governance policies, may be calculated at various levels of the dataset hierarchy (e.g., database, file, record, field).

In step 602, data analyzer 102 obtains the standard set of metrics at various levels of the dataset hierarchy, such as from database 104 storing the historical values for the metrics obtained from previously generated data artifacts. In one embodiment, the standard set of metrics is provided by a user. In one embodiment, the standard set of metrics corresponds to expected values for such metrics (e.g., value for a birthdate of person A), which may be based on previously recorded values for that same metric (e.g., previously recorded the value for the birthdate of person A from a document previously analyzed by data analyzer 102). In another embodiment, such expected values are obtained from previously aggregated data artifacts, such as obtaining the metric value of a social security number for person A. Such information is stored in database 104 to be later used by data analyzer 102 to determine the accuracy, consistency, completeness and relevancy of the health data.

In one embodiment, a hierarchical dataset includes data where observations fall into groups or clusters, where such hierarchies can have multiple levels.

In step 603, data analyzer 102 compares the calculated metrics with the standard set of metrics at various levels of the dataset hierarchy. For example, data analyzer 102 may perform an analysis, such as a trend analysis 702, to compare the calculated metrics 601 with the standard set of metrics (stored in database 104) at various levels of the dataset hierarchy. In such a manner, data analyzer 102 assesses the accuracy, consistency, completeness and relevancy of the health data. For example, the calculated metric of the birthdate of person A may be compared with the standard metric of the birthdate of person A to determine whether the calculated metric is within a threshold degree, which may be user-specified, of the expected value of the standard metric. If the calculated metric is not within a threshold degree of the expected value of the standard metric, then such health data may not be accurate, consistent, complete or relevant. Otherwise, such health data may be deemed to be accurate, consistent, complete and/or relevant.

In one embodiment, some parts of the monitoring process compare data extracts from similar source systems across different tenants. For example, Allscripts® is a common EHR platform among various tenants. Comparing statistical extracts of clinically relevant data from Allscripts® installations across tenants allows one to measure data quality differences and detect problems with the source data or data processing pipeline over time. In addition, comparing trend analysis at multiple stages in the pipeline across tenants allows automated troubleshooting of per-tenant configuration issues.

In step 604, data analyzer 102 produces the aggregate outputs based on the comparison of step 603. Such outputs may include classified trends 703, grouped datasets 704 and configured checklists 705.

With respect to classified trends 703, data analyzer 102 may first compute rollup trend values along several dimensions, such as EHR system, record type, etc., and for different time intervals (e.g., year/month/week to date). This results in a superset containing both the original single metric trends and the computed aggregate trends. Data analyzer 102 then classifies each trend using a set of mathematical tests. For example, trends may be classified as linear increasing, linear decreasing, bimodal, unstable, etc. In another example, one important classification is whether the trend changed suddenly with the most recent processing cycle.

With respect to grouped datasets 704, the source data can be grouped many ways, such as by record type (admission, diagnosis, observation, etc.), source system, or source system type. Embodiments of the present invention aggregate the trend classifications that were identified for each group (identified in classified trends 703) and identifies the trends for the group as a whole. For example, if several source systems exhibit increasing numbers of bad dates (e.g., dates in future or distant past), the user can identify a problem with the corresponding tenants' pipeline processing stages. However, if the trend only presents in a single data source, the user can recommend corrective action for that source (perhaps a default value is being saved).

With respect to configured checklists 705, a set of predefined checks is performed. For example, patient records which are not linked to a demographic record cannot be used by data analyzer 102. Patients with too many records linked to them (e.g., because they are test patients in the source system) may unbalance the distributed processing components, and as a result, they should be flagged.

By producing such aggregate outputs, the present invention ensures quality in the electronic health data.

Returning to FIG. 3, in conjunction with FIGS. 1-2 and 4-7, in step 304, data analyzer 102 generates a quality report 706 based on the aggregate outputs as shown in FIG. 7. Such a quality report 706 may include flagged issues with the datasets. For example, when a difference between a metric in the calculated set of metrics (see step 601) and a corresponding metric in the standard set of metrics (see step 602) exceeds a threshold variance, then such a metric is flagged in the quality report.

In one embodiment, the analysis output is combined into a series of reports 706 for end users across the organization. Some reports are specifically targeted to tenant users and focus on metrics pertaining to source data quality over various timeframes. Other reports are for internal use and focus on engineering metrics and detecting platform issues as they occur. FIGS. 8A-8B show a screen capture of a tenant-level data change report targeted toward internal users monitoring data quality changes across tenants in accordance with an embodiment of the present invention.

Returning to FIG. 3, in conjunction with FIGS. 1-2, 4-7 and 8A-8B, in step 305, data analyzer 102 presents the quality report to a user, such as the user of data analyzer 102.

Leveraging multitenancy for aggregate analytics from a scalable system-level framework enables the present invention to efficiently monitor large heterogeneous healthcare datasets from multiple hospital organizations. Furthermore, it also enables the present invention to monitor the multi-stage distributed platform which regularly processes new and existing source data.

Furthermore, the present invention improves the technology or technical field involving electronic health record systems. As discussed above, electronic health record systems generate electronic health records (EHRs). EHRs may include a range of data, including demographics, medical history, medication and allergies, immunization status, laboratory test results, radiology images, vital signs, personal statistics, such as age and weight, and billing information. Ensuring good data quality in such records is essential due to the types of information stored in such records which are used to ensure the wellbeing of patients. However, defining and measuring quality in such records is challenging, especially in a multitenant analytical platform (e.g., multiple healthcare systems), due to several factors, such as the large data volume. There are hundreds of millions of EHRs being generated every day from healthcare systems. Furthermore, defining and measuring quality in such records is challenging because of the heterogeneous data sources. Different hospitals often use distinctive EHR systems that adopt various formats. Even within the same hospital, different departments may generate duplicate or contradicting records. Thus, the standard of quality of EHR varies based on the data sources. Additionally, defining and measuring quality in such records is challenging because of complex relations among variables. For example, there are millions of codes from standard ontologies (International Classification of Diseases (ICD), Systematized Nomenclature of Medicine (SNOMED®), RxNorm®, Common Procedure Terminology (CPT®), Logical Observation Identifiers Names and Codes (LOINC®), etc.) that describe diagnoses, medical procedures, lab tests, and drugs, not to mention countless custom codes. Further, defining and measuring quality in such records is challenging because of operational factors, such as utilizing multiple data processing pipelines that are each configured per tenant, regularly receiving new data and utilizing a continuous delivery development model. These complications may introduce quality issues unrelated to the source data quality. Hence, there is not currently a means for ensuring quality in the electronic health data.

The present invention improves such technology by ensuring quality in the electronic health data by tracking and analyzing many quality metrics measured against the electronic health record datasets generated by electronic health record systems at multiple stages of the data processing pipelines. As a result, there is an improvement in the technical field of electronic health record systems.

The technical solution provided by the present invention cannot be performed in the human mind or by a human using a pen and paper. That is, the technical solution provided by the present invention could not be accomplished in the human mind or by a human using a pen and paper in any reasonable amount of time and with any reasonable expectation of accuracy without the use of a computer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for ensuring quality in electronic health data, the method comprising:
    monitoring multiple data processing pipelines, by a data analyzer, among different tenants for data artifacts generated from electronic health data comprising electronic health records from heterogeneous data sources thereby making it challenging to define and measure quality in said electronic health records, wherein each tenant is associated with a distinctive electronic healthcare system that generates electronic health records in a unique format that comprises codes from a unique ontology, wherein each tenant is associated with a different processing pipeline configured to receive said electronic health records in said unique format, wherein a standard of quality of said electronic health records varies based on said heterogeneous data sources, wherein said data processing pipelines comprise a set of data processing elements connected in series where an output of one element is an input of a next element, wherein said data processing pipelines comprise stages of different processing, wherein said generated data artifacts comprise tangible by-products produced during processing of electronic health record datasets as well as the datasets themselves, wherein said generated data artifacts comprise one or more of the following: unstructured health data, publishment of said unstructured health data in structured form, an intermediate form of health data formed by pre-processing of said structured health data and data store applications produced by applying standardized ontologies to said intermediate form of health data;
    aggregating, by said data analyzer, data artifacts of said generated data artifacts produced from a same stage of said data processing pipelines among said different tenants thereby comparing behavior across said datasets to flag unexpected changes;
    producing, by said data analyzer, a set of metrics at various levels of a dataset hierarchy from said aggregated data artifacts, wherein each of said set of metrics is a measurement of a particular characteristic of processing of electronic health data in a data processing pipeline for a tenant, wherein said produced set of metrics provides information about a quality of said electronic health data;
    analyzing, by said data analyzer, said produced set of metrics to generate aggregate outputs, wherein said aggregate outputs comprise each of the following: classified trends based on computing rollup values along several dimensions for different time intervals resulting in a superset containing both original single-metric trends and computed aggregate trends and then classifying each trend using a set of mathematical tests, grouped datasets by aggregating trend classifications identified in an output for each group and identified trends for said group as a whole, and configured checklists based on platform input limitations at each stage of said data processing pipelines among said different tenants, wherein by analyzing said produced set of metrics at multiple stages of said multiple data processing pipelines for multiple tenants to generate said aggregate outputs, quality in said electronic health records generated by different electronic healthcare systems is ensured;
    generating, by said data analyzer, a quality report based on said aggregate outputs, wherein said quality report comprises flagged issues with said datasets; and
    presenting, by said data analyzer, said quality report to a user.

2. The method as recited in claim 1 further comprising:
    calculating metrics at various levels of a dataset hierarchy from said aggregated data artifacts;
    obtaining a standard set of metrics at various levels of said dataset hierarchy;
    comparing said calculated metrics with said standard set of metrics at various levels of said data hierarchy to ensure quality in said electronic health data by assessing accuracy, consistency, completeness and relevancy of said electronic health data; and
    producing said aggregate outputs based on said comparison.

3. The method as recited in claim 2, wherein said standard set of metrics at various levels of said dataset hierarchy corresponds to historical values for metrics obtained from previously generated data artifacts.

4. The method as recited in claim 2, wherein a difference between a calculated metric and a corresponding metric in said standard set of metrics that exceeds a threshold variance is flagged in said quality report.

5. The method as recited in claim 1, wherein said produced set of metrics is calculated continuously as new data is ingested and as existing data is reprocessed.

6. The method as recited in claim 1, wherein each of said data processing pipelines among different tenants begins with an extraction of source system data and terminates with data store applications.

7. The method as recited in claim 1, wherein said quality report is customized for different user types.

8. A computer program product for ensuring quality in electronic health data, the computer program product comprising a computer readable storage medium having program code embodied therewith, the program code comprising programming instructions for:

monitoring multiple data processing pipelines, by a data analyzer, among different tenants for data artifacts generated from electronic health data comprising electronic health records from heterogeneous data sources thereby making it challenging to define and measure quality in said electronic health records, wherein each tenant is associated with a distinctive electronic healthcare system that generates electronic health records in a unique format that comprises codes from a unique ontology, wherein each tenant is associated with a different processing pipeline configured to receive said electronic health records in said unique format, wherein a standard of quality of said electronic health records varies based on said heterogeneous data sources, wherein said data processing pipelines comprise a set of data processing elements connected in series where an output of one element is an input of a next element, wherein said data processing pipelines comprise stages of different processing, wherein said generated data artifacts comprise tangible by-products produced during processing of electronic health record datasets as well as the datasets themselves, wherein said generated data artifacts comprise one or more of the following: unstructured health data, publishment of said unstructured health data in structured form, an intermediate form of health data formed by pre-processing of said structured health data and data store applications produced by applying standardized ontologies to said intermediate form of health data;

aggregating, by said data analyzer, data artifacts of said generated data artifacts produced from a same stage of said data processing pipelines among said different tenants thereby comparing behavior across said datasets to flag unexpected changes;

producing, by said data analyzer, a set of metrics at various levels of a dataset hierarchy from said aggregated data artifacts, wherein each of said set of metrics is a measurement of a particular characteristic of processing of electronic health data in a data processing pipeline for a tenant, wherein said produced set of metrics provides information about a quality of said electronic health data;

analyzing, by said data analyzer, said produced set of metrics to generate aggregate outputs, wherein said aggregate outputs comprise each of the following: classified trends based on computing rollup values along several dimensions for different time intervals resulting in a superset containing both original single-metric trends and computed aggregate trends and then classifying each trend using a set of mathematical tests, grouped datasets by aggregating trend classifications identified in an output for each group and identified trends for said group as a whole, and configured checklists based on platform input limitations at each stage of said data processing pipelines among said different tenants, wherein by analyzing said produced set of metrics at multiple stages of said multiple data processing pipelines for multiple tenants to generate said aggregate outputs, quality in said electronic health records generated by different electronic healthcare systems is ensured;

generating, by said data analyzer, a quality report based on said aggregate outputs, wherein said quality report comprises flagged issues with said datasets; and presenting, by said data analyzer, said quality report to a user.

9. The computer program product as recited in claim 8, wherein the program code further comprises the programming instructions for:

calculating metrics at various levels of a dataset hierarchy from said aggregated data artifacts;

obtaining a standard set of metrics at various levels of said dataset hierarchy;

comparing said calculated metrics with said standard set of metrics at various levels of said data hierarchy to ensure quality in said electronic health data by assessing accuracy, consistency, completeness and relevancy of said electronic health data; and producing said aggregate outputs based on said comparison.

10. The computer program product as recited in claim 9, wherein said standard set of metrics at various levels of said dataset hierarchy corresponds to historical values for metrics obtained from previously generated data artifacts.

11. The computer program product as recited in claim 9, wherein a difference between a calculated metric and a corresponding metric in said standard set of metrics that exceeds a threshold variance is flagged in said quality report.

12. The computer program product as recited in claim 8, wherein said produced set of metrics is calculated continuously as new data is ingested and as existing data is reprocessed.

13. The computer program product as recited in claim 8, wherein each of said data processing pipelines among different tenants begins with an extraction of source system data and terminates with data store applications.

14. The computer program product as recited in claim 8, wherein said quality report is customized for different user types.

15. A data analyzer, comprising:

a memory for storing a computer program for ensuring quality in electronic health data; and a processor connected to said memory, wherein said processor is configured to execute the program instructions of the computer program comprising:

monitoring multiple data processing pipelines among different tenants for data artifacts generated from electronic health data comprising electronic health records from heterogeneous data sources thereby making it challenging to define and measure quality in said electronic health records, wherein each tenant is associated with a distinctive electronic healthcare system that generates electronic health records in a unique format that comprises codes from a unique ontology, wherein each tenant is associated with a different processing pipeline configured to receive said electronic health records in said unique format, wherein a standard of quality of said electronic health records varies based on said heterogeneous data sources, wherein said data processing pipelines comprise a set of data processing elements connected in series where an output of one element is an input of a next element, wherein said data processing pipelines comprise stages of different processing, wherein said generated data artifacts comprise tangible by-products produced during processing of electronic health record datasets as well as the datasets themselves, wherein said generated data artifacts comprise one or more of the following: unstructured health data, publishment of said unstructured health data in structured form, an intermediate form of health data formed by pre-processing of said structured health data and data store applications produced by applying standardized ontologies to said intermediate form of health data;

aggregating data artifacts of said generated data artifacts produced from a same stage of said data processing pipelines among said different tenants thereby comparing behavior across said datasets to flag unexpected changes;

producing a set of metrics at various levels of a dataset hierarchy from said aggregated data artifacts, wherein each of said set of metrics is a measurement of a particular characteristic of processing of electronic health data in a data processing pipeline for a tenant, wherein said produced set of metrics provides information about a quality of said electronic health data;

analyzing said produced set of metrics to generate aggregate outputs, wherein said aggregate outputs comprise each of the following: classified trends based on computing rollup values along several dimensions for different time intervals resulting in a superset containing both original single-metric trends and computed aggregate trends and then classifying each trend using a set of mathematical tests, grouped datasets by aggregating trend classifications identified in an output for each group and identified trends for said group as a whole, and configured checklists based on platform input limitations at each stage of said data processing pipelines among said different tenants, wherein by analyzing said produced set of metrics at multiple stages of said multiple data processing pipelines for multiple tenants to generate said aggregate outputs, quality in said electronic health records generated by different electronic healthcare systems is ensured;

generating a quality report based on said aggregate outputs, wherein said quality report comprises flagged issues with said datasets; and presenting said quality report to a user.

16. The data analyzer as recited in claim 15, wherein the program instructions of the computer program further comprise:

calculating metrics at various levels of a dataset hierarchy from said aggregated data artifacts;

obtaining a standard set of metrics at various levels of said dataset hierarchy;

comparing said calculated metrics with said standard set of metrics at various levels of said data hierarchy to ensure quality in said electronic health data by assessing accuracy, consistency, completeness and relevancy of said electronic health data; and producing said aggregate outputs based on said comparison.

17. The data analyzer as recited in claim 16, wherein said standard set of metrics at various levels of said dataset hierarchy corresponds to historical values for metrics obtained from previously generated data artifacts.

18. The data analyzer as recited in claim 16, wherein a difference between a calculated metric and a corresponding metric in said standard set of metrics that exceeds a threshold variance is flagged in said quality report.

19. The data analyzer as recited in claim 15, wherein said produced set of metrics is calculated continuously as new data is ingested and as existing data is reprocessed.

20. The data analyzer as recited in claim 15, wherein each of said data processing pipelines among different tenants begins with an extraction of source system data and terminates with data store applications.

* * * * *